US012680095B2

(12) United States Patent　　(10) Patent No.:　US 12,680,095 B2
Gagnon　　　　　　　　　　　　　　(45) Date of Patent:　Jul. 14, 2026

(54) METHOD OF SINGLE STRAND RNA PURIFICATION EMPLOYING AN ANION EXCHANGER

(71) Applicant: Sartorius BIA Separations d.o.o., Ajdovscina (SI)

(72) Inventor: Peter S. Gagnon, Las Vegas, NV (US)

(73) Assignee: Sartorius BIA Separations d.o.o., Ajdovscina (SI)

( * ) Notice: Subject to any disclaimer, the term of this patent is extended or adjusted under 35 U.S.C. 154(b) by 941 days.

(21) Appl. No.: 17/918,242

(22) PCT Filed: Apr. 16, 2021

(86) PCT No.: PCT/EP2021/059911
　　§ 371 (c)(1),
　　(2) Date: Oct. 11, 2022

(87) PCT Pub. No.: WO2021/209601
　　PCT Pub. Date: Oct. 21, 2021

(65) Prior Publication Data
　　US 2023/0142167 A1　　May 11, 2023

(30) Foreign Application Priority Data

Apr. 17, 2020　(EP) .................................... 20170184

(51) Int. Cl.
　　*C12N 15/10*　　　　(2006.01)
(52) U.S. Cl.
　　CPC .................................. *C12N 15/101* (2013.01)
(58) Field of Classification Search
　　CPC .................................................. C12N 15/101
　　　　　　　　　　(Continued)

(56) References Cited

U.S. PATENT DOCUMENTS 10,138,475 B2　11/2018　Conrad
2005/0019814 A1　1/2005　Laugharn, Jr. et al.
(Continued)

FOREIGN PATENT DOCUMENTS

CN　　103993002 A　　8/2014
JP　　2007-500008 A　　1/2007
(Continued)

OTHER PUBLICATIONS

Easton et al., "Rapid, nondenaturing RNA purification using weak anion-exchange fast performance liquid chromatography", RNA, vol. 16, p. 647-653, (2010).
(Continued)

*Primary Examiner* — Madeline Gonzalez
(74) *Attorney, Agent, or Firm* — Christensen, Fonder, Dardi, Busse; Diane E. Bennett; Peter S. Dardi

(57) ABSTRACT

A method of single strand RNA purification employing an anion exchanger comprising the steps
　applying a sample containing single-stranded RNA to an anion exchanger,
　washing the anion exchanger at a first temperature in the range of 18° C. to 25° C. with a first salt solution having a first ionic strength in the range 0.5 M to 12.0 M,
　eluting the single stranded RNA by a second salt solution having a second ionic strength at a second temperature in the range of 35° C. to 80° C.,
with the proviso that the first ionic strength is at least 0.5 M higher than the second ionic strength.

17 Claims, 2 Drawing Sheets

| Method Step | Temperature | Concentration of Salt |
|---|---|---|
| equilibrate sample | ambient | any |
| equilibrate column | ambient | any |
| load-wash sample | ambient | any |
| high-salt wash | ambient | 0.5 M > than elution |
| low/no-salt wash | ambient | < 0.5 M |
| low/no-salt wash | elevated | < 0.5 M |
| elute | elevated | as required |

(58) Field of Classification Search
USPC ................................................ 210/660, 683
See application file for complete search history.

(56) References Cited

U.S. PATENT DOCUMENTS

| | | | |
|---|---|---|---|
| 2008/0076910 A1 | 3/2008 | Takkellapati et al. | |
| 2016/0024141 A1* | 1/2016 | Issa ........................ | G01N 30/96 |
| | | | 536/23.1 |

FOREIGN PATENT DOCUMENTS

| | | |
|---|---|---|
| JP | 2010-504738 A | 2/2010 |
| WO | 2009-100172 A1 | 8/2009 |
| WO | 2014-144767 A1 | 9/2014 |
| WO | 2017-182524 A1 | 10/2017 |
| WO | 2018-096179 A1 | 5/2018 |

OTHER PUBLICATIONS

Kanavarioti et al., "HPLC Methods for Purity Evaluation of Man-Made Single-Stranded RNAs", Scientific Reports, 9:1019, (2019).

Koubek et al., Strong anion-exchange fast performance liquid chromatography as a versatile tool for preparation and purification of RNA produced by in vitro transcription, RNA, vol. 19 No. 10, p. 1449-1459, (Oct. 2013).

Zlobina et al., "Efficient large-scale preparation and purification of short single-stranded RNA oligonucleotides", Biotechniques, vol. 60 No. 2, p. 75-83, (Feb. 2016).

Office Action from corresponding European Patent Application No. 20170184.4 dated Oct. 31, 2023.

Bautz et al., "Gene-specific messenger RNA: isolation by the deletion method", Science, vol. 151 Issue 3708, p. 328-330, (1966). (Abstract).

Office Action from corresponding Japanese Patent Application No. 2022-543191 dated May 20, 2025.

Baiersdörfer et al., "A Facile Method for the Removal of dsRNA Contaminant from In Vitro-Transcribed mRNA", Molecular Therapy Nucleic Acids, vol. 15, p. 26-35, (Apr. 2019).

Romanovskaya et al., "High-throughput purification of double-stranded RNA molecules using convective interaction media monolithic anion exchange columns", Journal of Chromatography A, vol. 1278, p. 54-60, (Feb. 22, 2013).

International Search Report for corresponding Patent Application No. PCT/EP2021/059911 dated Jul. 27, 2021.

* cited by examiner

| Method Step | Temperature | Concentration of Salt |
|---|---|---|
| equilibrate sample | ambient | any |
| equilibrate column | ambient | any |
| load-wash sample | ambient | any |
| high-salt wash | ambient | 0.5 M > than elution |
| low/no-salt wash | ambient | < 0.5 M |
| low/no-salt wash | elevated | < 0.5 M |
| elute | elevated | as required |

METHOD OF SINGLE STRAND RNA PURIFICATION EMPLOYING AN ANION EXCHANGER

CROSS REFERENCE TO RELATED APPLICATIONS

This application is a National Stage filing of PCT Application No. PCT/EP2021/059911 filed Apr. 16, 2021, entitled "A Method of Single Strand RNA Purification Employing an Anion Exchanger", which claims priority to European Patent Application No. 20170184.4, filed Apr. 17, 2020.

The present invention pertains to a method of single strand RNA purification employing an anion exchanger.

BACKGROUND

The use of anion exchange chromatography for purification of messenger RNA (mRNA) is known. Small constructs, such as those including 300 nucleotide bases or fewer can be purified on conventional anion exchangers [1] including strong anion exchangers employing quaternary amino ligands on a chromatographic solid phase, and including weak exchangers employing tertiary amino ligands on a chromatographic solid phase. Purification is most commonly conducted at roughly neutral pH (pH 6.0 to 8.0) and elution is performed with ascending gradients of sodium chloride or other salts.

Larger mRNA constructs, such as those including more than 300 bases have been shown not to elute from either strong or weak anion exchangers at ambient temperature, but they can be eluted if the operating temperature is sufficiently high, such as 65 degrees Celsius (65° C.) [2].

The technique of applying salts in a washing step before elution is known throughout the field of anion exchange chromatography, including for purification of proteins and DNA in addition to RNA. After applying the sample to the column, the column is washed with an elevated concentration of salt to cause weakly bound contaminants to be displaced and thereby removed from the surface of the ion exchanger. A known limitation with this approach is that the concentration of salt in the washing step must be lower than the amount of salt required to elute the product of interest [2]. If the salt concentration of the wash step encroaches too closely on the concentration required to elute the product of interest, some amount of the product will be removed along with the contaminants, potentially all of it.

Many different species of salts have been used or suggested for use with ion exchange chromatography, including for purification of RNA [2]. However, the need to maintain the salt concentration of a washing step below the concentration of salt required to elute mRNA remains. Chaotropic salts, sometimes referred to as denaturing salts, have been suggested to elute large mRNA from anion exchangers without requiring elevated operating temperature [2] but they have never been demonstrated to do so. As washing salts, they are understood to be constrained by the same concentration limits as all other salts: lower than the concentration of salt required to elute the mRNA.

SUMMARY

Subject matter of the invention is a method of single strand RNA purification employing an anion exchanger wherein
applying a sample containing single-stranded RNA to an anion exchanger, washing the anion exchanger at a first temperature with a first salt solution having a first ionic strength and,
eluting the single stranded RNA by a second salt solution having a second ionic strength at a second temperature, with the proviso that the first temperature is at least 5° C. lower than the second temperature and the first ionic strength is at least 0.5 M higher than the second ionic strength.

Typically, the first temperature can be defined as a temperature in the range of 18° C. to 25° C.

In one embodiment of the method of the invention the washing with the first salt solution can be conducted at an ionic strength in the range 0.5 M to 12.0 M greater, or 1 M to 10 M greater, or 2 M to 8 M greater, or 4 M to 6 M greater.

In another embodiment of the method of the invention the washing with the first salt solution can be conducted with a chaotropic salt, such as one or more from the group consisting of a guanidine salt, a perchlorate salt, a thiocyanate salt, or a mixture of salts.

In still another embodiment of the method of the invention the washing with the first salt solution may include a chelating agent at a concentration in the range of 1 mM to 1000 mM, or 5 mM to 500 mM, or 10 mM to 100 mM, or 20 mM to 50 mM.

In yet another embodiment of the method of the invention the washing with the first salt solution may include one or more species of chelating agents selected from the group consisting of ethylenediaminetetraacetic acid (EDTA), or ethylene glycol-bis(2-aminoethylether)-N,N,N',N'-tetraacetic acid (EGTA), and tris(2-aminoethyl)-amine (TREN).

In a further embodiment of the method of the invention the second salt solution employed for eluting the single-stranded RNA can be applied at the second temperature in the range of 35° C. to 80° C., or 45° C. to 70° C., or 50° C. to 70° C., or 55° C. to 70° C., or 60° C. to 70° C.

In still a further embodiment of the method of the invention the anion exchanger can be selected from the group consisting of a strong anion exchanger bearing quaternary amino ion exchange groups, a weak anion exchanger bearing tertiary amino ion exchange groups, a weak anion exchanger bearing secondary amino ion exchange groups, a weak anion exchanger bearing primary amino groups, an anion exchanger bearing more than one kind of amino groups.

Typically, the size of the RNA can be in the range of 1,000 bases to 25,000 bases.

In a preferred embodiment, it is a method of single strand RNA purification employing an anion exchanger comprising the steps
applying a sample containing single-stranded RNA to an anion exchanger,
washing the anion exchanger at a first temperature in the range of 18° C. to 25° C. with a first salt solution having a first ionic strength in the range 0.5 M to 12.0 M and,
eluting the single stranded RNA by a second salt solution having a second ionic strength at a second temperature in the range of 35° C. to 80° C.,
wherein the first ionic strength is at least 0.5 M higher than the second ionic strength.

The method of the present invention provides an improvement for purification of RNA, in particular mRNA, by anion exchange chromatography that directly violates the known rules for pre-elution washes in the field of ion exchange chromatography. It involves washing with salt concentrations that are substantially-to-dramatically higher than the salt concentration employed to elute the desired mRNA.

Further contrary to the known rules of pre-elution washes, the results are enhanced by the use of chaotropic salts, including at concentrations up to full saturation. Purification performance is further enhanced by inclusion of a chelating agent in the high-salt wash.

The method exploits the ability of such washes to remove the majority of proteins, DNA, and double-stranded RNA (dsRNA) from anion exchangers at ambient temperature without eluting the desired single-stranded mRNA (ssRNA). The ssRNA is later recovered by means of a salt gradient at an elevated operating temperature. By removing the majority of contaminants in advance of elution, the elution gradient can provide ultra-purification of ssRNA from the remaining trace levels of contaminants. Lacking this improvement, those contaminants would elute in the elution gradient, where they would be expected to compromise purity by overlapping to varying degrees with the desired ssRNA. The improvement is pertinent to purification of RNA of all sizes but especially to large and very-large mRNA, such as in the size range of 1,000-25,000 bases.

The performance improvement afforded by the method also enables a workflow simplification that rivals a technique known in the art as affinity chromatography. Affinity chromatography is a technique in which a biospecific ligand such as an antibody is covalently affixed to a solid phase. When a contaminated sample bearing the target of that antibody is applied to the solid phase, only the target molecule is captured while contaminants are eliminated by flowing through the column. After washing the column to rinse away trace levels of undesired species, the target molecule is eluted in a single highly purified fraction. In the present case, unpurified or partially purified sample containing ssRNA is loaded in high salt at ambient temperature. The majority of the contaminants flow through the solid phase. Highly purified ssRNA is eluted in a concentrated fraction during elution with a salt gradient at elevated temperature.

The present invention will be described in more detail in the following sections.

General Description of the Invention

In a general aspect, the invention is a solid phase extraction method for removal of contaminants and impurities from a preparation containing single-stranded messenger RNA (ssRNA).

In a specific aspect, the invention is related to purification of ssRNA by anion exchange chromatography, where contaminants are eliminated by a high-salt wash at ambient temperature and ssRNA is later eluted by a salt gradient to a lower concentration of salt at an elevated operating temperature.

In one embodiment, the original sample containing ssRNA and contaminants consists of one from the group of an invitro transcription mixture, the resuspended precipitate after precipitation of an in vitro transcription mixture by a salt or by an organic solvent, or a chromatography fraction from a previous purification step. Accordingly, the relative purity of the ssRNA may be very crude with ssRNA representing only a small fraction of the total biomolecule content, or it may be highly purified with ssRNA representing the dominant proportion of the total biomolecule content. Among such samples, contaminant species may include dsRNA; DNA and/or DNA fragments remaining after in vitro transcription of the ssRNA; proteins including the enzymes used to promote in vitro transcription; and hetero-aggregates or complexes containing multiple contaminant species that became stably associated during in vitro transcription, or which were already present in the DNA plasmid or within the enzyme preparations used to perform in vitro transcription.

In one embodiment, the anion exchanger is a strong anion exchanger such as quaternary amine anion exchanger. In a closely related embodiment, the anion exchanger is a weak anion exchanger such as a tertiary amine anion exchanger. In an another closely related embodiment, the weak anion exchanger is a secondary amine anion exchanger. In another closely related embodiment, the weak anion exchanger is a primary amine anion exchanger. In another closely related embodiment, the anion exchanger may be of mixed character, including two or more kinds of amine derivatives.

In one embodiment, ambient temperature at which the salt wash is applied may be defined as a temperature within the range of 18° C. to 25° C. or 20° C. to 22° C.

In one embodiment, the elevated operating temperature at which the ssRNA is eluted may be within the range of 35° C. to 85° C., or 40° C. to 80° C., or 45° C. to 75° C., or 50° C. to 70° C., or 55° C. to 65° C., or a value within a lower range, or within an intermediate range, or within a higher range.

In one embodiment, the concentration of salt in the pre-elution high-salt wash at ambient temperature exceeds the eluting concentration of salt at elevated operating temperature by 0.5 M to 12 M, or 1.0 M to 10 M, or 2.0 M to 8.0 M, or 3.0 M to 6.0 M.

In one embodiment, the species of salt in the pre-elution high-salt wash at ambient temperature is the same as the species of salt used to elute the ssRNA at elevated operating temperature.

In another embodiment, the species of salt in the pre-elution high-salt wash at ambient temperature is different than the species of salt used to elute the ssRNA at elevated operating temperature.

In a related embodiment, the species of salt in the pre-elution high-salt wash is a chaotropic salt and the species of salt used to elute the ssRNA is a neutral salt. In one such embodiment, the chaotropic salt is one from the group of a guanidinium salt, a thiocyanate salt, a perchlorate salt, or a combination thereof. In another such embodiment, the species of neutral salt used to elute the ssRNA is sodium chloride, or potassium chloride, or sodium acetate, or potassium acetate. In another such embodiment, the species of salt used to elute the ssRNA is a chaotropic salt.

It will be recognized by experienced persons in the art that RNA may be precipitated by high concentrations of neutral salts such as sodium chloride or potassium chloride, as well as by others such as lithium chloride. Precipitation would likely compromise chromatographic performance inside a chromatographic device. Elution with a non-precipitating salt, such as a chaotropic salt, may therefore support better chromatographic performance such as sharper eluting peaks, higher resolution, and higher recovery of the desired ssRNA. It will also be recognized by experienced persons in the art that if it is desired to avoid the use of a chaotropic salt for elution, the operating temperature may be elevated further to reduce the concentration of a neutral salt required to elute the desired ssRNA.

In one embodiment, the pre-elution high-salt wash includes a chelating agent. In one such embodiment, the chelating agent may be ethylenediaminetetraacetic acid (EDTA) at a concentration of 2 mM to 200 mM, or 5 mM to 100 mM, or 10 mM to 50 mM, or 20 mM to 25 mM, or a lower range, or intermediate range, or higher range up to full saturation. In closely related embodiments, the chelating agent may be a salt of citric acid, or phosphoric acid, or ethylene glycol-bis(2-aminoethylether)-N,N,N',N'-tetraacetic acid (EGTA), or tris(2-aminoethyl)amine (TREN), or another chelating agent, or a mixture of chelating agents over the same range of concentrations described for EDTA.

In one embodiment, the pre-elution high-salt wash is followed by a low-salt or no-salt wash so that the ssRNA remains bound to the anion exchanger as the operating temperature is increased from ambient to the elevated operating temperature selected for elution of the ssRNA.

In one embodiment, an anion exchanger at ambient temperature may be equilibrated to any pH in the range of pH 3.0 to 9.0 for the step of binding the ssRNA. The sample may also contain any species of salt, with a concentration in the range of 0.0 M to full saturation. It will generally be preferable to equilibrate the anion exchanger to a pH close to neutrality, such as in the range of pH 6.5 to pH 7.5 and containing a neutral salt such as sodium chloride at a concentration of about 50 mM to about 100 mM. In a related embodiment, the sample may be equilibrated to conditions approximating those to which the anion exchanger is equilibrated. In a different related embodiment, the column and the sample are equilibrated to different salt and pH conditions.

In one embodiment, the method commences at ambient temperature. The anion exchanger is equilibrated with a buffer of roughly neutral pH and either no additional salt or a low concentration of a neutral salt. The sample containing ssRNA may be titrated to the same approximate range of conditions then filtered to remove solids. The sample is then applied to the anion exchanger, after which the anion exchanger is rinsed with equilibration buffer to displace unbound contaminants from the interstitial spaces within the body of the anion exchanger. A pre-elution high-salt wash buffer containing a chelating agent is applied at about the same pH as the equilibration buffer. The majority of proteins, DNA, and dsRNA that were bound under the original equilibration conditions are dissociated from the surface of the anion exchanger and rinsed from the column. The column is washed again with the original equilibration buffer to remove the high salt and chelating agent. The operating temperature is elevated and the ssRNA is eluted by increasing the salt concentration.

In a different embodiment commencing at ambient temperature, the anion exchanger is equilibrated with a buffer of the same composition intended to perform the pre-elution high-salt wash. In one such embodiment, the sample is equilibrated in advance to contain the same species and concentrations of salts intended to perform the pre-elution high salt wash. In such an embodiment, it will be recognized that the majority of contaminants will fail to bind to the anion exchanger. Trace levels of unbound contaminants remaining in the interstitial spaces of the column can be washed away after loading by application of the pre-elution high-salt wash buffer. The column can then be washed with a low-salt or no-salt buffer so that the desired ssRNA remains bound to the anion exchanger while the temperature is elevated and the ssRNA is eluted by increasing the salt concentration It will be recognized by persons of experience in the art that the two preceding embodiments represent variations of each other, both employing the same key principle, specifically that the high salt wash results in the majority of contaminants being unbound by the anion exchanger.

The method of the invention may be practiced using any device which is customary in the art, e. g. the anion exchanger can be arranged in a chromatography device. Typically, the solid phase surface can be in the form of a monolith, a column of packed particles, a column of packed nanofibers, a membrane adsorber, or a hydrogel, among other chromatography formats.

The method of the invention may be preceded by, or followed by, or both, by one or more additional processing methods to purify the ssRNA to a greater degree than can be achieved by any single processing method alone.

DETAILED DESCRIPTION OF THE INVENTION

Figures 1, 2:
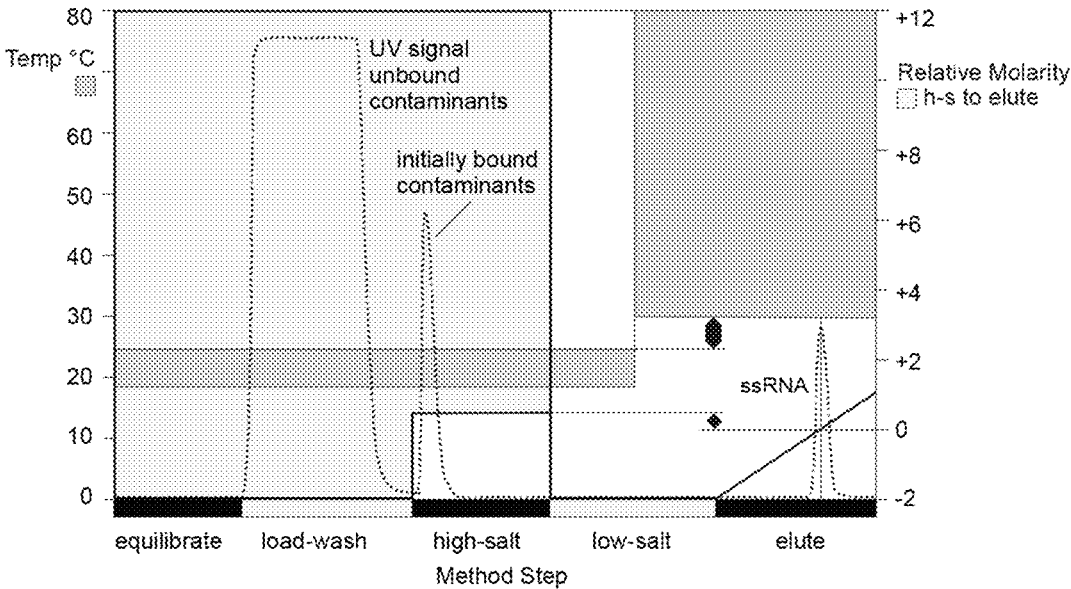
FIG. 1 diagrams and tabulates the steps of performing the invention and highlights examples of the range of operating temperatures and salt concentrations for each.
FIG. 2 diagrams the steps of performing the invention and graphically illustrates the range of operating temperatures and salt concentrations for each.
Figure 3:
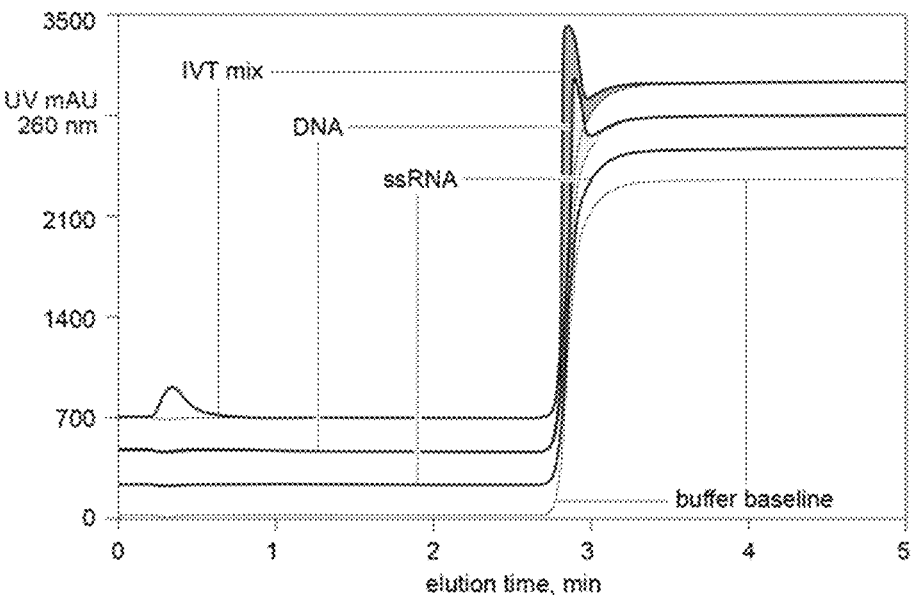
FIG. 3 depicts the effect of a high-salt guanidine-EDTA wash on the binding of ssRNA, DNA, and an in vitro transcription mixture containing contaminating proteins DNA, and mRNA.

The term "RNA" refers to ribonucleic acid.

The term "mRNA" refers to messenger RNA.

The term "in vitro transcription" refers to the chemical process by which mRNA is synthesized artificially from a DNA template, often referred to as a DNA plasmid. In vitro transcription mixtures also require that the raw materials for mRNA synthesis be present in the form of nucleotide bases. The enzyme to perform the actual synthesis must also be present. After completion of in vitro transcription, the DNA template becomes a contaminant that must be removed, as do the enzymes that were added to promote synthesis. Any contaminants that were present in the DNA plasmid preparation or in the enzyme preparations must also be removed.

The term "ssRNA" refers to single-stranded mRNA.

The term "dsRNA" refers to double-stranded mRNA. Undesired subpopulations of dsRNA are produced during in vitro transcription in addition to the desired ssRNA. Undesired dsRNA species spontaneously form post-transcription by intrachain interaction of complementary sequences within the base-strand. Formation of dsRNA sequences can also occur by pairing with complementary sequences among neighboring ssRNA molecules, thereby creating non-specific interchain dimers and higher order multimers that may also contain intrachain ds sequences. Double-stranded RNA triggers an unwanted and potentially lethal immune response when injected into a subject, making its removal a particular object of purification.

The term "RNA size" or "size of RNA" refers to the number of nucleotide bases in the strand. Nucleotide bases are commonly noted as "b". Thus, the designation 1000b refers to an RNA strand of nucleotide 1000 bases.

The term "anion exchanger" refers to a solid phase suitable for performing chromatography that bears positively charged groups on its surface(s). Positively charged groups on anion exchangers typically consist of amino groups of various types.

The most common type of anion exchanger is commonly referred to as a strong anion exchanger. It consists of quaternary amino groups covalently affixed to the surface of the chromatographic solid phase. Strong anion exchangers are widely available commercially and commonly have names like Q, QA, QAE, etc., where the Q refers to the quaternary. Strong anion exchangers are so called because the maintain their full charge over a wide range of pH values such as from pH 3 to pH 12.

The second most common type of anion exchanger consists of weak anion exchangers, including solid phases bearing tertiary amines as diethylaminoethyl (DEAE) groups. Weak exchangers are so called because they start to lose charge at the upper end of the pH range.

Weak anion exchangers bearing primary amino groups are also known and available commercially. One example is marketed under the name Toyopearl NH2-750F, manufactured by Tosoh Biosciences, where "NH2" refers to the primary amine [https://www.separations.eu.tosohbioscience.com/solutions/process-media-products/by-mode/ion-exchange/anion-exchange/toyopearl-nh2-750f]. Marketing materials indicate that the primary amino groups are in the form of a polyamine, meaning that it is a polymer with repeating primary amine subunits affixed covalently to the solid phase. Such polymers are typically linked to the surface of the solid phase through one or more of their primary amino groups. This linkage has the effect of converting the linking amino residues from primary amino groups to secondary amino groups, thereby producing a mixture of primary amino groups and secondary amino groups on the surface of the solid phase.

Another example of a weak anion exchanger is manufactured by Sartorius under the name Sartobind STIC PA, where "PA" refers to the primary amine [www.sartorius-.com/shop/ww/en/usd/sartobind-stic®-pa/c/M_Sartobind-_STIC_PA]. Marketing materials indicate that the primary amino group is in the form of a polymer, specifically polyallylamine, with repeating primary amino subunits, affixed covalently to the solid phase. As with the previous product, such polymers are typically linked to the surface of the solid phase through one or more of its primary amino groups. This linkage has the effect of converting the linking amino residues from primary amino groups to secondary amino groups, thereby producing a mixture of primary amino groups and secondary amino groups on the surface of the solid phase.

Another example of a weak anion exchanger is manufactured by J. T. Baker under the name Bakerbond PolyPEI and marketed through VWR [in.vwr.com/store/product/21666435/ion-exchange-chromatography-media-j-t-baker-bakerbond]. A solid phase surface bearing polyethylene-imine (PEI) represents an example of a solid phase dominated by secondary amino groups but still including primary amino groups. Linear PEI polymers bear primary amino groups at their termini but secondary amino groups at each repeating node of the linear polymer. Branched PEI polymers have a higher proportion of primary amino groups since there is one at the terminus of every branch, however there is also a tertiary amine at the base of every branch.

Another example of a weak anion exchanger is manufactured by BIA Separations under the name CIMmultus EDA, where EDA refers to ethylene diamine [www.biaseparations.comien/products/monolithic-columns/products-for-preparative-applications/111/eda-aexactivated]. Solid phase surfaces bearing EDA represent a balance of primary amino groups and secondary amino groups, slightly favoring secondary amines.

The anion exchanger may be a chromatographic solid phase in the form of one or more porous membranes, one or more nanofibers, one or more porous or non-porous particles, or a monolithic solid phase, including monoliths synthesized from a single polymer mixture, or so-called hydrogels which represent monoliths synthesized first as a macro-skeleton with a secondary ligand-bearing polymer phase synthesized on top of it. Any of these solid phase materials may be provided in a housing to facilitate performance of chromatography. Chromatographic solid phases in housings are commonly referred to as chromatographic devices and often as columns.

The term "equilibrated" or "equilibration" refers to a chemical conditioning step performed on the solid phase and/or on the sample to create a specific chemical environment. Solid phases are customarily conditioned by exposing them to a buffer that embodies the desired pH and salt composition. Samples are customarily conditioned by titration of pH, sometimes by dilution, and sometimes by buffer exchange techniques including by chromatography, or by dialysis, or by diafiltration with tangential flow filtration membranes. All of these methods and the criteria for choosing one or another are known in the art.

The term "sample loading" or "sample application" or "column loading" refers to the process of bringing the equilibrated sample into contact with the equilibrated positively charged solid phase dominantly bearing primary amino groups. This is usually done with chromatography devices by causing the sample to pass through the device by means of an external force, such as by gravity or by pumping.

The term "adsorption" refers to the process of binding a biological product to a chemically complementary surface. Adsorption is distinct from absorption, which can be likened to uptake of water by a sponge through the physical action of capillarity but not involving a chemical interaction. Complementarity in the case of anion exchangers is understood to involve electrostatic charge. For example, the negative electrostatic charge on the surface of RNA mediates its adsorption to the surface of a positively charged solid phase. Adsorption of biological products to chromatographic solid phases is often referred to by the more familiar term "binding".

The term "selective adsorption" refers to conditions that permit adsorption of at least one species while preventing adsorption of one or more other species. In the present case, operating conditions may be adjusted to prevent the binding of contaminants while permitting ssRNA to bind.

The term "desorption" refers to the process of releasing a biological product from a chemically complementary surface to which it has been previously adsorbed. For the method of the invention, desorption of ssRNA will require the presence of salt at an elevated operating temperature.

The term "selective desorption" refers to situations in which one or more adsorbed species are released from the solid phase surface by a change in the conditions that leaves one or more other species still adsorbed. A yet-different set of conditions can then be applied to release a different subset of species from the solid phase surface. In one such instance, the majority of contaminants might be removed from the anion exchanger by application of a high concentration of salt while ssRNA remains bound. The contaminants would be said to have been selectively desorbed. The ssRNA would be selectively desorbed in a follow-on elution step with salt at an elevated operating temperature.

The term "washed" traditionally refers to a process of exposing the loaded column to clean buffer for the purpose of displacing unbound species from pores or channels within the device. The term "rinsed," in the present context, has the same meaning. In the most basic case, the wash buffer has the same formulation as the equilibration buffer. The traditional use of wash buffers sometimes employs a washing step with a higher concentration of salt than used to load the sample but at a lower concentration than required to elute the desired product from the solid phase.

The term "pre-elution high-salt wash" or "high-salt wash", in the context of the method of the invention, fulfills the fundamentally different role of chemically releasing contaminants from the solid phase that would not be released by a traditional salt-wash step. This is enabled by applying the high-salt wash at ambient temperature where the salts are not able to elute the ssRNA.

The term "low-salt wash" or "no-salt" wash refers to a wash conducted after the pre-elution high-salt wash to remove the salts in advance of raising the operating temperature, so that the ssRNA remains bound while the temperature is being raised. The low-salt wash is understood to contain less salt than necessary to elute ssRNA at the selected elevated operating temperature.

The term "elution" represents a special case of the term "desorption" pertinent to the field of chromatography. In the present case, it refers to a process of changing the chemical environment in which anion exchanger resides in order to disrupt the interaction between the solid phase and ssRNA so that the ssRNA can be recovered.

Elution may be conducted in one or a series of steps in which each step disrupts the interaction between the anion exchanger and the ssRNA to a greater extent. Changes in conditions may also be made in a gradual, continuous, or linear manner. Whether in a step or linear format, changes in operating conditions are commonly referred to as gradients and particularly as elution gradients. Step gradients are often considered more convenient but linear gradients typically support better reproducibility.

The term "chaotropic salt" refers to a salt species for which at least one of its constituent ions has a high chaotropic ranking in the Hofmeister series of lyotropic and chaotropic ions. Lyotropic ions reside at one end of the Hofmeister series. Chaotropic ions populate the opposite end of the series. Chaotropic ions are often described as being preferentially bound by biomolecules. Chaotropic salts have the effect of relaxing non-covalent interactions within and among biomolecules, sometimes to the extent of destabilizing overall structure and dissociating interactions among the respective elements in multicomponent noncovalent mixtures. They usually have the effect of increasing solubility and rarely or never cause precipitation. Examples of chaotropic salts include guanidinium salts, thiocyanates, and perchlorates, among others. In some cases, both the anion and cation of a particular salt are strongly chaotropic as in the case of guanidine thiocyanate. Such salts have more chaotropic potential than salts including only a chaotropic anion or chaotropic cation. Lyotropic ions reside at the opposite end of the Hofmeister series. They are often described as being preferentially excluded by biomolecules. Lyotropic ions have the effect of stabilizing biomolecules, favoring non-specific association among individual elements of mixtures. Strongly lyotropic ions usually decrease solubility of large biomolecules, and often cause precipitation. Examples of lyotropic salts include ammonium sulfate, potassium phosphate, and sodium citrate, among others. Salts that represent intermediates in the Hofmeister series include so-called neutral salts such as sodium chloride, potassium chloride, sodium acetate, and potassium acetate. Their influence on proteins is mediated predominantly through coulombic (electrostatic) forces. Their effects on solubility and stability of proteins tends to mild but they substantially depress solubility of mRNA, causing it to precipitate at high salt concentrations.

The term "multivalent metal cation" refers the positively charged ionic form of a metal where the net charge of the ion is two or greater. Multivalent metal cations include calcium, magnesium, and zinc, all of which have a net charge of 2+, and ferric iron with a net charge of 3+, among others with similar or different valencies. All of these ions have an affinity for nucleic acids which they bind through coordination bonds. Coordination bonds are 15-60 times stronger than ionic bonds, which means that binding of multivalent metal cations to nucleic acids or other biomolecules persists even at saturating concentrations of salts. Multivalent metal cations can be problematical in the purification of RNA because they can promote formation of dsRNA sequences or stabilize existing dsRNA sequences. They can also promote formation of complexes or stabilize existing complexes (associations), among multiple RNA molecules, between RNA and DNA molecules, and among RNA, DNA, and protein contaminants.

The term "chelating agent," in the context of the method of the invention, refers to a molecule with the ability to form such strong coordination bonds with multivalent metal cations that they are able to competitively remove those metal ions from previous associations with biomolecules, including nucleic acids, including mRNA. Examples of chelating agents include ethylenediaminetetraacetic acid (EDTA), ethylene glycol-bis(2-aminoethylether)-N,N,N',N'-tetraacetic acid (EGTA), tris(2-aminoethyl)amine (TREN), phosphoric acid, and citric acid.

The term "complexes" or "associations" or "heteroaggregates" refers to aggregations among multiple species of biomolecules through non-specific chemical interactions by their various surface chemical features. Non-specific chemical interactions that promote and maintain the stability of complexes include electrostatic interactions, hydrogen bonding, hydrophobic interactions, and coordination bonding. Through these interactions, RNA can form stable complexes with DNA and proteins. Such complexes often have properties similar to the desired product. They accordingly represent Trojan Horses that smuggle contaminants into what should be the pure ssRNA elution fraction, even though the properties of the independent contaminants should preclude that possibility.

Given effective extraction of multivalent metal cations, effective dissociation of nucleic acid-protein complexes can be achieved with high concentrations of chaotropic salts such a guanidinium salts, and to a lesser degree with high concentrations of non-chaotropic salts such as NaCl. Lyotropic salts are likely to impose a contrary influence.

High-salt washes offer the possibility to dissociate these complexes so that their constituent contaminants are easier to remove. The complex-dissociative of chaotropic salts is greater than neutral salts and much greater than lyotropic salts. The presence of chelating agents further aids to dissociate complexes by eliminating multivalent metal cation linkages among the individual constituents of a complex.

The term "nuclease" or "nuclease enzyme" refers to proteins that have the ability to cleave the chains of nucleic acids, ideally into individual nucleotides, doublets, or triplets. There are two major classes: DNAse enzymes that lyse DNA, and RNAase enzymes that lyse RNA. RNAses are to be strictly avoided because they will destroy the ssRNA product. DNAses are often used to simplify purification by destroying the DNA plasmid template used to produce mRNA. DNAse enzymes frequently require the use of a multivalent metal cation co-factor to function properly. Multivalent metal cations can interfere with RNA purification as discussed above.

The term "protease" or "proteinase" or "proteolytic enzyme" refers to a protein that has the ability cut other proteins into small fragments. This is sometimes used as a method of reducing protein contamination ahead of chromatography steps that might be burdened by such contamination. Many proteases, such as trypsin require a multivalent metal cation co-factor to function properly. Multivalent metal cations can interfere with RNA purification as noted above. Proteases commonly employed for this purpose include proteinase K which provides good results even in the absence of a multivalent metal cation co-factor.

The following series of general non-limiting descriptions of basic method options illustrates variations in how the method may be performed and provides a platform for more detailed discussion of operational variables. It is understood that the buffer conditions mentioned in each of these scenarios are intended to provide a general idea of how the method may be practiced and that optimization of buffer formulations will typically be required to best accommodate a given sample. This is understood among persons of experience in the art since each ssRNA may be of a different size. There may be variation in the concentration of the ssRNA. There will certainly also be differences in the identities and proportions of contaminants present in the sample.

In one embodiment, a strong anion exchanger in the form of a chromatography device such as a QA monolith is equilibrated at ambient temperature to a pH value close to neutrality, such as 20 mM Tris, 100 mM sodium chloride, pH 7.5±0.5. An in vitro transcription mixture is equilibrated similar pH, salt, and temperature. It is filtered to remove solids if necessary, then applied to the anion exchanger. The anion exchanger is then washed with 20 mM Tris, 3 M guanidine-HCl, 20 mM EDTA, pH 7.5±0.5. The high-salt chelating wash is followed with a wash by the original equilibration buffer to remove the excess salt and chelating agent. The operating temperature is reset to 65° C. and the anion exchanger is eluted with a linear salt gradient of 50 device volumes, starting from the equilibration buffer and gradually transitioning to an endpoint buffer of 20 mM Tris, 1.5 M sodium chloride, pH 7.5±0.5. The anion exchanger may then be cleaned and sanitized by application of a buffer containing 1 M sodium hydroxide.

In a different embodiment, a weak anion exchanger in the form of a chromatography device such as a DEAE monolith is equilibrated at ambient temperature with 20 mM Tris, 3 M guanidine-HCl, 20 mM EDTA, pH 7.5±0.5. Guanidine is added to an in vitro transcription mixture to a final concentration of 3 M. EDTA is added to the in vitro transcription mixture to a final concentration of 20 mM. The pH of the in vitro transcription mixture is optionally adjusted to a pH pH 7.5±0.5 the filtered, if necessary to remove solids. The sample is applied to the anion exchanger then washed with equilibration buffer until UV absorbance reaches baseline. The anion exchanger is washed with 20 mM Tris, 100 mM sodium chloride to clear the guanidine and EDTA. The operating temperature is re-set to 65° C. and the anion exchanger is eluted with a linear salt gradient of 50 device volumes, starting from the equilibration buffer and gradually transitioning to an endpoint buffer of 20 mM Tris, 1.5 M sodium chloride, pH 7.5±0.5. The anion exchanger may then be cleaned and sanitized by application of a buffer containing 1 M sodium hydroxide.

It will be recognized by persons of experience in the art that the two preceding embodiments represent variations of each other, both employing the same key principle, specifically that the high salt wash results in the majority of contaminants being unbound by the anion exchanger.

In a closely related embodiment, the anion exchanger is a weak anion exchanger. In one such embodiment, the weak anion exchanger is one from the group consisting of a tertiary amine anion exchanger, a secondary amine anion exchanger, a primary amine anion exchanger, or a weak anion exchanger containing a mixture of primary amino groups and secondary amino groups, or a mixture of primary amino groups and secondary amino groups and tertiary amino groups.

In another closely related embodiment, the sample is an in vitro transcription mixture that has been treated with a salt to precipitate the mRNA and the mRNA has been resuspended by another by a buffer in which the mRNA is soluble. In another closely related embodiment, the sample is an in vitro transcription mixture that has been treated with an organic solvent to precipitate the mRNA and the mRNA has been resuspended by another by a buffer in which the mRNA is soluble. In another closely related embodiment, the sample is an in vitro transcription mixture that has been treated with a DNAse enzyme to fragment the DNA plasmid template from which to transcribe the mRNA. In another closely related embodiment, the sample is an in vitro transcription mixture that has been treated with a protease enzyme to fragment proteins. In another closely related embodiment, the sample is an in vitro transcription mixture that has been treated with a DNAase enzyme and then a protease enzyme. In another closely related embodiment, the sample is a chromatography fraction from a prior purification step.

In another closely related embodiment, the operating pH is pH 7.0±0.5. In a similar closely related embodiment, the operating pH is pH 6.5±0.5. In a similar closely related embodiment, the operating pH is pH 8.0±0.5.

In another closely related embodiment, the salt employed in the equilibration buffer may be potassium chloride, or sodium acetate, or potassium acetate. In one such embodiment, the salt concentration of the equilibration buffer may be a value in the range of 0 mM to 500 mM, or 10 mM to 250 mM, or 50 mM to 100 mM.

In another closely related embodiment, the salt species of the high-salt wash buffer is guanidine thiocyanate, or sodium thiocyanate, or potassium thiocyanate, or potassium perchlorate, or sodium perchlorate, or sodium chloride, or potassium chloride. In one such embodiment, the salt concentration of the high-salt wash buffer is greater than the amount of salt required to elute the ssRNA at elevated temperature by 0.5 M to 10.0 M, or 1.0 M to 8.0 M, or 2.0 M to 6.0 M, or 3.0 M to 4.0 M. It will be recognized that some salts will not be soluble at extremely high concentrations and their concentration limits must therefore be lower than the concentration at which they become saturated. It will also be recognized that the highest salt concentration possible may more efficiently remove contaminants but that the improvement in performance may be minor past a certain point. In such cases, it will be appropriate to reduce the concentration to the lowest level that achieves adequate clearance of contaminants as judged by the user. In many embodiments, the preferred concentration of the salt wash will be in the range of 3.0 M to 4.0 M. It will be further recognized that, in most cases, chaotropic salts will produce more desirable results.

In another closely related embodiment, the concentration of EDTA in the high salt wash buffer is a value within the range of 5 mM to saturation, or 10 mM to 1000 mM, or 20 mM to 500 mM, or 50 mM to 100 mM. In another closely related embodiment, the chelating agent is EGTA, or TREN. Chelating agents such as phosphoric acid and citric acid may be employed, however their status as strongly lyotropic anions in the Hofmeister series suggests that they may provide inferior results. In one embodiment, chelating agents are absent from the high-salt wash. In one embodiment, a chelating agent is the salt used to perform the high-salt wash. In one embodiment, chelating agents are used in every step of the process. In one embodiment, chelating agents are used in only some step of the process. In one embodiment, different concentrations of the same chelating agent are used in different process steps. In one embodiment, different chelating agents or mixtures of chelating agent as used in different process steps.

In another closely related embodiment, the species of salt used to elute the ssRNA at an elevated operating temperature, may be potassium chloride, or sodium acetate, or potassium acetate, or a salt of lysine, or a salt of histidine, or a salt arginine, or a salt of guanidine, or a thiocyanate salt, or a perchlorate salt, or a combination of salts. In some such embodiments, the inclusion of a nonionic additive with strong hydrogen-donor capacity may be included, such as sorbitol, xylitol, mannitol, trehalose, sucrose, or another sugar or combination of sugars with the intent to reduce the salt concentration at which the ssRNA elutes. In some such embodiments, the concentration of sugar may be in the range of 1% to 20%. In other such embodiments, urea may be employed with the same intention as a sugar, where the concentration of urea is in the range of 1 M to 10 M.

A particular benefit of the invention is that its ability to remove DNA plasmids from ssRNA preparations makes it unnecessary to perform nuclease digestion of an in vitro transcription mixture, or partially purified in vitro transcription mixture. This has disproportionately high value because nuclease digestion requires addition of magnesium ions in order for the enzyme to be active. Those magnesium ions potentially contribute to cross-linking of the desired ssRNA, with itself and with other sample components, with the practical result that the recovery of the desired ssRNA product may be reduced. By making nuclease digestion unnecessary, addition of magnesium ions becomes unnecessary, and recovery of ssRNA is uncompromised.

In one embodiment, the method of the invention may be combined with the method of affinity chromatography using an Oligo dT (OdT) ligand. The two methods may be combined in any sequence desired.

In one embodiment, the method of the invention may be combined with the method of hydrophobic interaction chromatography (HIC). The two methods may be combined in any sequence desired. In one such embodiment, the hydrophobic ligand on the HIC solid phase may consist of a phenyl group. In another such embodiment, the hydrophobic ligand on the HIC solid phase may consist of a butyl group. In another such embodiment, the hydrophobic ligand on the HIC solid phase may consist of a hexyl group. In other such embodiments, the hydrophobic ligand on the HIC solid phase may consist of a different aliphatic or aromatic group, or a group that embodies both aliphatic and aromatic properties.

In one embodiment, the method of the invention may be combined with the method of reverse phase chromatography (RPC). The two methods may be combined in any sequence desired. In one such embodiment, the hydrophobic nature of the solid phase surface may be conferred by the native hydrophobicity of the styrene divinylbenzene (SDVB) polymer used to synthesis the solid phase. In another such embodiment, the hydrophobic nature of the solid phase surface may be conferred by the hydrophobicity of a ligand affixed to the surface of the solid phase, where that ligand represents an aliphatic hydrocarbon, or an aromatic hydrocarbon, or a ligand of mixed aliphatic-aromatic character.

In one embodiment, the method of the invention may be combined with the method of hydroxyapatite chromatography. The two methods may be combined in any sequence desired.

In one embodiment, the method of the invention may be combined with affinity chromatography using an OdT ligand and with RPC. The three methods may be performed in any sequence desired. In related embodiments, the method of the invention may be combined with any other two methods, or more.

All references cited herein are incorporated by reference to the full extent to which the incorporation is not inconsistent with the express teachings herein.

The invention is further explained by the following non-limiting examples.

EXAMPLES

Example 1. Elimination of DNA bound to a strong anion exchanger by means of a high-salt wash. A strong (quaternary amino) anion exchange monolith was equilibrated with 50 mM Tris, pH 7.5 at 20° C. A sample consisting of plasmid DNA (5000 bp) such as used as a template for in vitro transcription of mRNA was injected at 20° C. The monolith was washed with equilibration buffer at 20° C., then a high-salt wash containing 50 mM Tris, 20 mM EDTA, 3.0 M guanidine-HCl, pH 7.5 at the same temperature. A low-salt wash containing 50 mM Tris, pH 7.5 was applied at 20° C. to wash out the guanidine and EDTA. The operating temperature was elevated to 65° C. and the anion exchanger was eluted with a linear gradient to 20 mM Tris, 2.0 M sodium chloride, pH 7.5. The ion exchanger was cleaned with 1.0 M sodium hydroxide, 2.0 M sodium chloride. The DNA applied to the anion exchanger bound upon injection and remained bound during the wash with equilibration buffer. It eluted in the high salt wash. In a separate experiment, a reference buffer baseline was created by repeating the conditions except omitting injection of any sample. The portions of the chromatograms representing column equilibration, sample injection, wash with equilibration buffer, and the leading portion of the high-salt wash are illustrated in FIG. 1. DNA is indicated by the light gray shaded area.

Example 2. Elimination of contaminants from an in vitro transcription mixture containing DNA, proteins, and mRNA by means of a high-salt wash. The conditions of Example 1 were repeated except substituting an in vitro transcription mixture in place of the DNA sample described in example 1. Unbound contaminants passed through the anion exchanger immediately after injection. Bound contaminants were dissociated from the column by the high-salt wash, causing them to elute. The portions of the chromatograms representing column equilibration, sample injection, wash with equilibration buffer, and the leading portion of the high-salt wash are illustrated in FIG. 1. Contaminants removed by the high-salt wash are indicated by the dark gray shaded area. As shown in the Figure, the amount of contaminants removed by the wash is larger than the amount of DNA removed in example 1. This is an indication of the higher contaminant content of the in vitro transcription mixture, including DNA, dsRNA, and proteins.

Example 3. Persistence of ssRNA binding to a strong anion exchanger during a high-salt wash. The conditions of Examples 1 and 2 were repeated except substituting a sample containing an ssRNA ladder containing ssRNA of sizes ranging from 200b to 6000b. The ssRNA bound upon injection, remained bound during the wash with equilibration buffer and remained bound during the high-salt wash. The portions of the chromatograms representing column equilibration, sample injection, wash with equilibration buffer, and the leading portion of the high-salt wash are illustrated in FIG. 1. Note that the UV profile strictly parallels the profile of the baseline, in contrast to examples 1 and 2 where the removal of contaminants was evident in the shaded peaks. The ssRNA was subsequently eluted in the in the salt gradient at 65° C.

REFERENCES

[1] A Romanovskaya, L P Sarin, D H Bramford, M M Poranen, High-throughput purification of double-stranded R.N.A. molecules using convective interaction media monolithic anion exchange columns, J. Chromatography A, 1278 (2013) 54-60.
[2] WO 2014/144767 A1

All references cited herein are incorporated by reference to the full extent to which the incorporation is not inconsistent with the express teachings herein.

The invention claimed is:

1. A method of single strand RNA purification employing an anion exchanger comprising the steps of:

applying a sample containing single-stranded RNA to an anion exchanger, washing the anion exchanger at a first temperature in the range of 18° C. to 25° C. with a first salt solution having a first ionic strength in the range of 0.5 M to 12.0 M, eluting the single stranded RNA by a second salt solution having a second ionic strength at a second temperature in the range of 35° C. to 80° C., with the proviso that the first ionic strength is at least 0.5 M higher than the second ionic strength.

2. The method claim 1 wherein the washing with the first salt solution is conducted at an ionic strength in the range of 1 M to 10 M.

3. The method of claim 1 wherein the washing with the first salt solution is conducted with a chaotropic salt.

4. The method of claim 3 wherein the chaotropic salt is selected from the group consisting of a guanidine salt, a perchlorate salt, a thiocyanate salt, and mixtures thereof.

5. The method of claim 1 wherein the washing with the first salt solution includes a chelating agent at a concentration in the range of 1 mM to 1000 mM.

6. The method of claim 1 wherein the washing with the first salt solution includes one or more species of chelating agents selected from the group consisting of ethylenediaminetetraacetic acid (EDTA), or ethylene glycol-bis(2-aminoethylether)-N,N,N',N'-tetraacetic acid (EGTA), and tris(2-aminoethyl)amine (TREN).

7. The method of claim 1 wherein the second salt solution employed for eluting the single-stranded RNA is applied at the second temperature in the range of 45° C. to 70° C.

8. The method of claim 1 wherein the anion exchanger is selected from the group consisting of a strong anion exchanger bearing quaternary amino ion exchange groups, a weak anion exchanger bearing tertiary amino ion exchange groups, a weak anion exchanger bearing secondary amino ion exchange groups, a weak anion exchanger bearing primary amino groups and an anion exchanger bearing more than one kind of amino groups.

9. The method of claim 1 wherein the size of the RNA is in the range of 1,000 bases to 25,000 bases.

10. The method claim 1 wherein the washing with the first salt solution is conducted at an ionic strength in the range of 2 M to 8 M.

11. The method claim 1 wherein the washing with the first salt solution is conducted at an ionic strength in the range of 4 M to 6 M.

12. The method of claim 1 wherein the washing with the first salt solution includes a chelating agent at a concentration in the range of 5 mM to 500 mM.

13. The method of claim 1 wherein the washing with the first salt solution includes a chelating agent at a concentration in the range of 10 mM to 100 mM.

14. The method of claim 1 wherein the washing with the first salt solution includes a chelating agent at a concentration in the range of 20 mM to 50 mM.

15. The method of claim 1 wherein the second salt solution employed for eluting the single-stranded RNA is applied at the second temperature in the range of 50° C. to 70° C.

16. The method of claim 1 wherein the second salt solution employed for eluting the single-stranded RNA is applied at the second temperature in the range of 55° C. to 70° C.

17. The method of claim 1 wherein the second salt solution employed for eluting the single-stranded RNA is applied at the second temperature in the range of 60° C. to 70° C.

\* \* \* \* \*